(12) United States Patent
Kiesel et al.

(10) Patent No.: US 12,201,464 B2
(45) Date of Patent: Jan. 21, 2025

(54) MOBILE COMPUTED TOMOGRAPHY SYSTEM

(71) Applicant: Siemens Healthineers AG, Forchheim (DE)

(72) Inventors: Jan-Christoph Kiesel, Bayreuth (DE); Julia Busch, Kemnath (DE); Georg Walberer, Kastl (DE); Johannes Koch, Kemnath (DE); Fabian Strobl, Erbendorf (DE); Guido Schraml, Schwarzenbach (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 204 days.

(21) Appl. No.: 17/954,956

(22) Filed: Sep. 28, 2022

(65) Prior Publication Data

US 2023/0102393 A1   Mar. 30, 2023

(30) Foreign Application Priority Data

Sep. 30, 2021  (DE) .................... 10 2021 210 937.3
Oct. 26, 2021  (DE) .................... 10 2021 212 036.9

(51) Int. Cl.
*A61B 6/00* (2024.01)
*A61B 6/03* (2006.01)
(52) U.S. Cl.
CPC ............ *A61B 6/4405* (2013.01); *A61B 6/035* (2013.01); *A61B 6/4435* (2013.01); *A61B 2560/0214* (2013.01)

(58) Field of Classification Search
CPC ..... A61B 6/4405; A61B 6/035; A61B 6/4435; A61B 2560/0214
See application file for complete search history.

(56) References Cited

U.S. PATENT DOCUMENTS

| | | | |
|---|---|---|---|
| 6,519,312 B1 | 2/2003 | Duffy et al. | |
| 2006/0120511 A1 | 6/2006 | Gregerson et al. | |
| 2013/0140447 A1* | 6/2013 | Kim .................... | A61B 6/035 248/371 |
| 2020/0016927 A1 | 1/2020 | Dietrich et al. | |

FOREIGN PATENT DOCUMENTS

DE     102018211669 B4    1/2020

OTHER PUBLICATIONS

Bittel O. P.D., HTWG Konstanz, [Online]. Available: http://www-home.htwg-konstanz.de/~bittel/ain_robo/Vorlesung/03_Roboterkinematik.pdf. [Zugriff am Nov. 26, 2020].
KLOCKE Fritz "Fertigungsverfahren 4 Umformen", 6. Auflage, Springer Verlag, 2017.

* cited by examiner

*Primary Examiner* — Kiho Kim
(74) *Attorney, Agent, or Firm* — Harness, Dickey & Pierce, P.L.C.

(57) ABSTRACT

A mobile computed tomography system has a gantry with an opening for at least partially accommodating a patient, and a carriage configured to be moved over a substrate with motor assistance. The gantry is arranged on an upper side of a support frame of the carriage. The support frame includes at least one shaped profile tube.

19 Claims, 6 Drawing Sheets

MOBILE COMPUTED TOMOGRAPHY SYSTEM

CROSS-REFERENCE TO RELATED APPLICATION(S)

The present application claims priority under 35 U.S.C. § 119 to German Patent Application No. 10 2021 210 937.3, filed Sep. 30, 2021, and German Patent Application No. 10 2021 212 036.9, filed Oct. 26, 2021, the entire contents of each of which are incorporated herein by reference.

FIELD

One or more example embodiments of the present invention relate to a mobile computed tomography (CT) system which enables computed tomography recordings of a patient to be carried out at any desired location, that is, in a transportable manner. This is desirable, particularly in emergency admissions by hospitals or for mobile ambulances. For this purpose, the mobile CT system has a trolley and/or a carriage for changing the position of the CT system. With regard to production times, production costs, weight and modularity, the CT system according to one or more example embodiments of the present invention has an optimized carriage construction.

BACKGROUND

In known mobile CT systems, a gantry of a CT scanner comprising imaging components such as an X-ray source and an X-ray detector is arranged on the carriage. The carriage therefore serves as a mobile base for a CT scanner. It is also known to permanently install a CT scanner comprising a substructure designed therefor in an ambulance.

Previously known trolley designs are characterized by a complex structure with a plurality of components and therefore partially unnecessary internal interfaces and require a high level of, particularly manual, assembly effort. Largely therein, edge-bent steel sheet parts are used, which are welded to one another.

Secondly, due to the complexity of the construction, an adaptation of the trolley design to, for example, specific customer wishes or restricted environment conditions is made more difficult and requires many design changes in each case. For example, in known trolley designs, wheels and drives cannot be exchanged without design changes. Their production is complex and expensive due to a large number of manual processing steps.

SUMMARY

It is an object of one or more example embodiments of the present invention to provide a mobile computed tomography system with an improved carriage construction which overcomes the described disadvantages. In particular, it is an object of one or more example embodiments of the present invention to provide a simple, modular, cost-effective and lightweight carriage construction for the mobile CT system.

At least this object is achieved by way of a mobile computed tomography system according to one or more example embodiments of the present invention. Preferred and/or alternative, advantageous embodiment variants are also described.

One or more example embodiments of the present invention relate to a mobile computed tomography system. This comprises a gantry with an opening for at least partial accommodation of a patient and a carriage movable over a substrate with motor assistance. The gantry is therein arranged on an upper side of a support frame of the carriage. The support frame is configured comprising at least one shaped profile tube.

The computed tomography system has a recording unit comprising imaging components, specifically at least one X-ray source and at least one X-ray detector in each case which cooperate to generate a computed tomography recording and/or a plurality of X-ray projections to form a computed tomography recording. The recording unit is arranged around a central opening in the gantry. The opening is configured to receive a patient at least partially therein. Preferably, the opening of the gantry is configured to receive the head of the patient. For example, the opening can have a diameter in the range between 25 cm and 45 cm, in particular between 30 cm and 35 cm, for example 33 cm. The recording unit is designed to rotate about a system axis, typically the patient longitudinal axis, during the recording. The at least one X-ray source emits X-rays during the recording, which pass through body regions of the patient situated at least in the opening and thereby are attenuated and are incident as projection data on the at least one X-ray detector.

In a preferred embodiment, the operating element is arranged on a rear side, that is, a side facing away from an advancing direction of the CT system. In this way, the operating person is situated substantially behind the CT system during a displacement movement of the CT system and can visually monitor the movement initiated by the operating element.

In other implementations of the present invention, the carriage is designed to be installed permanently on a substrate, in particular in an ambulance. Here, no movement control and/or an operating element for the input of travel commands is provided.

The carriage of the CT system has a support frame which is designed to support the gantry completely. The gantry of the CT system according to one or more example embodiments of the present invention is arranged on an upper side of the support frame. According to one or more example embodiments of the present invention, the gantry is therefore situated above the support frame.

One or more example embodiments of the present invention are based upon the recognition that a particularly simple, weight-reducing and cost-reducing design of the support frame can be achieved in that the support frame is constructed via at least one shaped profile tube. In preferred embodiments, the support frame comprises a plurality of shaped profile tubes. In further embodiments, the support frame consists entirely of shaped profile tubes.

Shaped profile tubes are standardized pre-shaped workpieces and/or semifinished products which are produced cost-effectively and with high availability and high dimensional accuracy in mass production. Shaped profile tubes are obtainable in a great variety of dimensions, in particular thicknesses and lengths and are therefore very easily adaptable to the requirements of a mobile CT system with regard to form stability and carrying capacity.

In a preferred embodiment of the computed tomography system, the support frame comprises three shaped profile tubes extending parallel to and spaced from one another, oriented parallel to the advancing direction of the carriage. In other words, the support frame comprises three shaped profile tubes which are oriented to one another and/or to a system axis along the advancing direction. The shaped profile tubes are preferably designed as hollow profiles with a defined wall thickness. Hollow profiles have a high strength and/or stiffness with an advantageously low weight.

The three (first) shaped profile tubes are preferably arranged in a plane, in particular in a plane parallel to the substrate. The two outer shaped profile tubes can therein each form outer sides of the support frame and the central shaped profile tube preferably crosses the center of the support frame. In some embodiments, the two outer shaped profile tubes can thus define the dimension of the carriage in the spatial direction extending transversely to the advancing direction. The three shaped profile tubes preferably have the same spacing from one another. The three shaped profile tubes preferably have the same edge dimension and the same wall thickness and/or the same profile shape. The use of identical parts can advantageously reduce production and storage costs.

In a further advantageous embodiment of the computed tomography system, the three shaped profile tubes are connected via two further shaped profile tubes extending parallel to and spaced apart from one another, which are also preferably designed as hollow profiles. The two further shaped profile tubes preferably extend transversely, that is perpendicularly to the three first shaped profile tubes. The two further shaped profile tubes are also preferably designed with the same profile shape and the same edge dimension as well as the same wall thickness. Preferably, the two further shaped profile tubes are fastened at least on one side to ends of the three first shaped profile tubes, wherein the ends of the three first shaped profile tubes on this side lie in a plane extending perpendicularly to the substrate. The two further shaped profile tubes are also preferably arranged in one plane.

In further embodiments of the computed tomography system, the three (first) shaped profile tubes have a rectangular profile and the two further shaped profile tubes have a U-profile. In particular, the three first shaped profile tubes have a square profile, but can also be configured as a rectangular profile. A U-profile tube differs from a rectangular profile tube in that one longitudinal side of the tube is designed to be open, whereas in a rectangular profile tube, all four tube longitudinal sides are closed.

Preferably, the rectangular profile tubes are designed with an edge dimension of between 6 cm and 10 cm, in particular 8 cm×8 cm. The U-profile tubes can have an edge dimension in the range from 5 cm to 12 cm. The shaped profile tubes preferably have the same wall thickness, specifically a wall thickness in the range from 3 mm to 7 mm, in particular 4 mm.

Preferably, the shaped profile tubes are produced as steel components.

The connection between the shaped profile tubes is preferably produced by welding. Other alternative or additional joining techniques such as screw fastening, riveting, gluing or the like can also be utilized.

By way of the design of the support frame with standard shaped profiles, the advantages of identical parts can be exploited in the production of the carriage. In addition thereto, the design of the support frame with standard shaped profiles enables a support frame construction with a high degree of stability and/or carrying capacity with simultaneously low weight. In addition, the support frame construction according to one or more example embodiments of the present invention, enables a high degree of accessibility and many empty spaces between the shaped profile tubes which can advantageously be used for further components of the carriage, in particular cable guides and/or supply lines without increasing the space requirements of the carriage and/or the CT system. According to one or more example embodiments of the present invention, the plan area of the CT system is approximately 70 cm×140 cm, wherein the carriage can have a height of approximately 120 cm.

In a further implementation of the computed tomography system, the U-profile tubes are arranged above the rectangular profile tubes and with a longitudinal side opened toward the substrate. According to one or more example embodiments of the present invention, cut-outs can be provided at the joining sites in the longitudinal sides adjoining the open longitudinal side of the U-profile tubes, which at least partially reproduce the profile shape of the rectangular profile. These cut-outs can be introduced particularly easily into the U-profile tubes via corresponding post-processing steps, for example by milling or cutting, in the longitudinal sides of the U-profile tube.

The longitudinal sides of the U-profile tubes that are upwardly directed, that is in the direction of the gantry, are consequently closed. In further advantageous implementations of the computed tomography system, the upwardly directed longitudinal sides and/or profile sides of the U-profile tubes are designed for receiving a linear guideway for a gantry frame carrying the imaging components of the gantry. Therein, the gantry frame is arranged along the U-profile tubes in a displaceable manner relative to the carriage.

In contrast to stationary CT systems, in which for example, for a spiral scan of the patient, the movement takes place via a defined table advance in the opening of the gantry along the system and/or patient longitudinal axis, for a comparable scan with a mobile CT system, the imaging components of the gantry must be moved relative to the patient. For this purpose, firstly, the entire CT system can be moved along the substrate relative to the patient. Alternatively, only the imaging components are displaced relative to the carriage. According to one or more example embodiments of the present invention, it is provided that the imaging components are arranged such that they are able to rotate (about the opening in the gantry) on a gantry frame, also called the drum, wherein the gantry frame is designed to be displaceable relative to the carriage and/or relative to the support frame. For this purpose, the upwardly directed U-profile longitudinal sides are used. These are each designed to receive a linear guideway for the gantry frame.

Accordingly, for example, a guide rail can be mounted directly on each of the upwardly directed profile sides of the U-profile tubes, in which corresponding guide elements of the gantry frame engage. In this way, the gantry frame is designed to carry out a linear movement along the U-profile tubes relative to the carriage and/or its support frame and to displace the imaging components during an imaging recording relative to the patient along its longitudinal axis.

In further embodiments of the present invention, further linear guideways can be provided on the two U-profile tubes, which also cooperate with components of the gantry, in particular housing parts of the gantry that are telescopically displaceable relative to one another in order to bring about a linear displaceability of the housing parts along the system axis. Alternatively, more than two, for example four, further U-profile tubes can be provided which are also arranged parallel to one another and to the two further U-profile tubes and open in the direction of the substrate and are connected, as described above, to the three rectangular profile tubes, wherein then each upwardly directed U-profile longitudinal side is designed for receiving a linear guideway for a component of the gantry in order to displace the components relative to the carriage and/or the support frame.

In these embodiments, the present invention also utilizes the support frame construction to realize the linear displacement movement of gantry components. In this way, the component complexity of the CT system is advantageously reduced.

In a preferred development of the computed tomography system, the two U-profile tubes are connected via at least two transverse struts, each forming, centrally between the two U-profile tubes, a bearing bushing for a recirculating ball screw for displacing the gantry frame. The at least two transverse struts are preferably arranged transversely to the two U-profile tubes and in the same plane as the U-profile tubes. The transverse struts can preferably also be configured as standard shaped profile components. In some embodiments, the transverse struts preferably extend above and/or closely beside and parallel to two of the three rectangular profile tubes. The transverse struts can also be designed as steel components.

Provided in each of the transverse struts is an opening formed as a bearing bushing, by way of which the respective recirculating ball screw of a ball screw drive is guided and mounted. The nut of the recirculating ball screw is preferably coupled to the gantry frame at a central attachment point. The nut and thus the gantry frame is displaced along the linear guideways by way of the rotation of the recirculating ball screw. The recirculating ball screw is preferably coupled at one end to a motor drive unit which can be actuated, for example, via the control unit when a CT scan is carried out. In some embodiments, more than two transverse struts can also be provided between the U-profile tubes. The ball screw drive, that is the actuating unit, can then advantageously be arranged, supported and/or mounted between the U-profile tubes of the support frame.

In these embodiments, the present invention does not only utilize the support frame construction also for realizing the linear displacement movement of gantry components, so that the component complexity is further reduced, but it also uses the free spaces within the support frame construction for arranging further carriage components, so that overall, the installation space required can be reduced.

In a preferred implementation of the computed tomography system, at least one of the three rectangular profile tubes forms, at its end arranged in the advancing direction of the carriage, a seating for at least one wheel arrangement. In other words, according to one or more example embodiments of the present invention, the rectangular profiles are used for the wheel mounting and/or chassis mounting. In particular, the at least one wheel arrangement provided in the advancing direction comprises wheel elements functioning as front wheels of the CT system. In this way, the component complexity of the CT system can also be further reduced. In some embodiments, the centrally arranged rectangular profile tube can form the seating for the wheel arrangement. These embodiments of the CT system then preferably comprise three wheels. In other embodiments, the two outer rectangular profile tubes can form seatings for wheel arrangements. These embodiments of the CT system then preferably comprise four wheels. In some embodiments, all three rectangular profile tubes can form a seating for a wheel suspension.

If a rectangular profile tube forms a wheel suspension, the rectangular profile tube is preferably designed, in the advancing direction, that is on the side of the CT system opposite the operating element, to be longer than the other rectangular profile tubes. The one rectangular profile tube forming a wheel suspension then forms a projection from the remaining support frame of the carriage directed in the advancing direction and/or forwardly. In other words, at least this rectangular profile tube protrudes forwardly beyond the front U-profile tube. The wheel suspension seatings of a plurality of, in particular both, outer rectangular profile tubes can also be designed to support a wheel suspension together. The seating for the wheel arrangement in a rectangular profile tube is formed, for example, by at least one exactly fitting and exactly positioned opening, cut-out, bore, specifically formed contact and/or support area or suchlike in the forwardly protruding region of the profile tube, which can be introduced via a few conventional post-processing steps such as drilling, milling, cutting or welding (on) into one of the longitudinal sides of the rectangular profile tube. Preferably, the seating of the at least one rectangular profile tube is arranged in an upwardly or laterally oriented longitudinal side of the rectangular profile tube.

One or more example embodiments of the present invention enable an adaptation of the support frame to differently designed wheel arrangements purely by way of adaptations in relation to the wheel arrangement seating in at least one of the rectangular profiles. The remaining frame construction remains largely untouched on a change of the wheel arrangement. Thus, the present CT system is able to be adapted particularly easily to specific customer wishes and/or specific environmental conditions and, in particular, can be retrofitted in the field in relation to the chassis design.

In an alternative, immovable embodiment of the present invention, the support frame comprises no wheel arrangement, but rather further connecting pieces designed as bent sheet metal elements for firm attachment of the support frame to the substrate. The connecting pieces can comprise corresponding contact and/or support areas or regions with which they can be anchored to the substrate. The further bent sheet metal elements are preferably fixed beneath, that is on the longitudinal sides, preferably the undersides of the rectangular profile tubes of the support frame. By way of a simple addition of the further bent sheet metal elements in place of wheel arrangements, the support frame construction can also be adapted for immovably installed uses of the CT system such as, for example, in an ambulance.

In further advantageous embodiments of the computed tomography system, the wheel arrangement comprises at least one wheel element which is designed as a passive and/or driven wheel element. A wheel element can be designed as a roll, wheel, drum, cylinder element or suchlike or can comprise at least one such, that is, also a plurality thereof. The carriage is moved over the substrate in that the at least one wheel element rolls over the substrate, in contact therewith. A passive wheel element should be understood to be a wheel element which is moved not directly by way of a motor drive, but on propulsion of the carriage, passively tracks the direction and/or velocity. A passive wheel element can be designed, for example, as a tracking roller which can be designed with or without a degree of freedom of rotation about its vertical axis. An active wheel element should be understood to be a wheel element which has a motor drive via which both a drive rotary moment and/or a desired movement direction for the wheel element can be set. An active wheel element within the meaning of the present invention is also to be a wheel element which can be braked and/or blocked actively, that is on the basis of and/or via a control command specified for example via the operating element or by the operating person.

To this extent, the carriage can have at least one wheel element designed in the form of one or two passive tracking rollers, in the form of one or two tracking rollers that are able to be steered and/or blocked or in the form of one or two wheels that are able to be steered and motor-driven or suchlike. In this way, different drive concepts can be realized, for example, a linear movement capability via a differential drive. Alternatively, an areal mobility can also be realized.

For this purpose, in a particularly preferred embodiment of the computed tomography system, the at least one wheel element is designed as an omnidirectional wheel. An omnidirectional wheel is characterized by a plurality, for example eight, preferably nine, roller elements arranged about a wheel axis which can be motor-driven such that a movement can be carried out from a standstill in any desired direction. In particular, the CT system has a plurality of omnidirectional wheels, at least three, for example, four omnidirectional wheels. This design enables a particularly high degree of maneuverability of the CT system since, in this way, for example a direction change by the CT system about a defined rotation point can be achieved, which enables deployment in a restricted environment. In this embodiment, the turning circle of the CT system is defined solely by the dimensions of the carriage itself.

In some embodiments of the present invention, the wheel arrangement can comprise a fixing element. This preferably acts in the region of the wheel suspension and the substrate and increases the stability of the computed tomography system when standing. By this mechanism and/or means, vibrations which can be transmitted by internal or external influences to the rotating part of the gantry can be prevented or at least reduced. The fixing element is, for example, designed comprising at least one hydraulic strut which extends in the vertical direction and can be driven in and out with length changes. In this way, the fixing element can bring about a fixed, stable position of the carriage, including for passive wheel elements, which is important, in particular, for a high quality image data capture by imaging components moved rotationally about the system axis and/or translationally along the U-profile tubes.

In some embodiments of the present invention, the fixing element can also be designed as an electrically or mechanically driven linear drive or a scissor lift.

In alternative embodiments, the fixed positioning of the CT system can be achieved for example via active wheel elements that can be blocked and/or braked.

In further alternative embodiments, the chassis construction and the intrinsic weight of the CT system of approximately 1 metric ton are sufficient per se for a stable position.

In a further implementation of the computed tomography system, the wheel arrangement comprises at least one spring element which supports the at least one wheel element against the support frame. The spring element serves to dampen vibrations and/or loading via the wheel element into the support frame occurring during bumpy travel, that is travel over an uneven substrate. This advantageously brings about a component protection and increases the lifespan of the carriage.

Preferably, more than one spring element can be provided. Preferably, all the wheel elements have at least one spring element. The spring element is configured in a preferred embodiment as a helical spring. In some embodiments, the wheel element can be fixed on a holding element of the wheel arrangement which is suspended, in relation to the support frame, such that it can rotate against the spring tensioning force of the spring element.

In alternative embodiments, the wheel arrangement comprises no spring element. In these embodiments, impact loads during bumpy travel are conducted directly and completely into the support frame or can be absorbed via the treads on the wheel elements.

In combination with an omnidirectional drive, in place of one or more spring elements or in addition thereto, a swing axle can also be provided, on which omnidirectional wheels can be arranged. The swing axle advantageously enables a compensation for height differences of the substrate between two wheels mounted on the swing axle.

In a further implementation of the computed tomography system, a further seating for a wheel arrangement is arranged on each of the ends, lying opposite to the wheel arrangement seating, of at least two rectangular profile tubes, wherein the further wheel arrangement seatings are constructed in a bent sheet metal element for receiving a motor.

The support frame thus comprises a bent sheet metal component which is fastened to the side of the carriage facing the operating element, for example, on at least two, preferably three rectangular profile tubes. In a preferred embodiment, the bent sheet metal component has at least one exactly fitting and exactly positioned opening, cut-out, bore, specifically formed contact and/or support area for each wheel arrangement seating, on which the wheels, in particular the rear wheels, of the CT system can be suspended. In particular, the wheel elements of this at least one wheel arrangement are active, that is motor-driven, wheels.

In a preferred embodiment, the bent sheet metal component functions simultaneously as a motor seating, and/or a drive seating. In other words, the motor and/or further drive components such as wheel axles, gear units or suchlike are at least partially accommodated in and/or beneath the sheet metal component.

The bent sheet metal component forming the bent sheet metal element can be joined in a per se known manner to the remaining support frames, for example, via a welded or screw fastened connection. The sheet metal component can be designed, for example, as a punched steel component with a thickness of 3 mm to 4 mm, which is bent in at least one post-processing step to be precisely fitting. The sheet metal component can be supported at least partially with additional strengthening elements for increased stability.

In a further advantageous implementation of the computed tomography system, the bent sheet metal element is further designed to carry a housing for receiving the control unit of the computed tomography system. The housing can advantageously also form an operating tower of the CT system on which the operating element for manual input of movement commands can be arranged. In other words, in some embodiments, the housing of the control unit and/or the operating tower is connected via the bent sheet metal element to the support frame. For this purpose, the bent sheet metal element can comprise corresponding contact and/or seating areas for the housing of the control unit.

In a further advantageous implementation of the computed tomography system, at least one battery compartment is arranged beneath the rectangular profile tubes. In a preferred embodiment, this is oriented transversely to the advancing direction of the carriage and is constructed to be accessible on at least one short side. The at least one battery compartment can also be configured as a bent sheet metal element which is punched via conventional processing steps from a steel sheet and is subsequently pressed into shape. The battery compartment can be designed as a push-in compartment or as a battery drawer. As a push-in compartment, the battery compartment can be fixed beneath the rectangular profile tubes and corresponding sliding and/or running surfaces can be provided for easy pushing in and/or for the removal and/or exchange of a battery. As a battery drawer, the battery compartment is itself arranged mounted beneath the rectangular profile tubes able to slide or roll. For the removal and/or replacement of the battery, the whole battery drawer is now pulled laterally out of the support frame. This advantageously simplifies access to the battery.

BRIEF DESCRIPTION OF THE DRAWINGS

The above-described properties, features and advantages of this invention and the manner in which they are achieved are made more clearly and distinctly intelligible with the following description of the exemplary embodiments which are set out in greater detail making reference to the drawings. This description entails no limitation of the present invention to these exemplary embodiments. In different figures, the same components are provided with identical reference signs. The figures are, in general, not to scale. In the figures.

DETAILED DESCRIPTION

Figure 1:
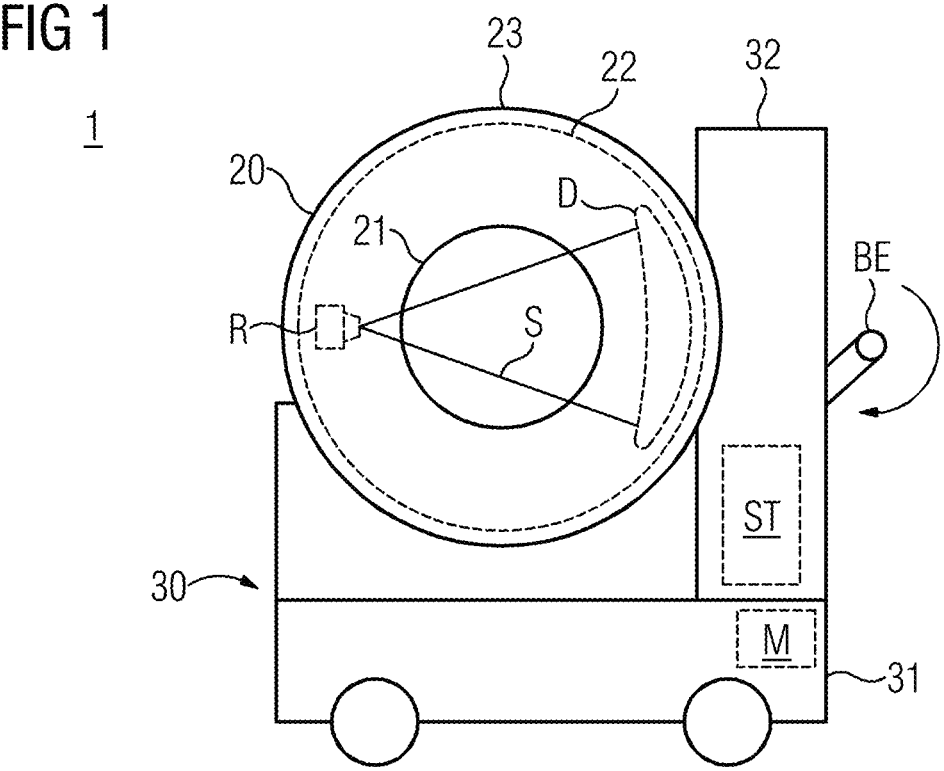
FIG. 1 shows a schematic view of a mobile computed tomography system in one embodiment of the present invention.

FIG. 1 shows a schematic view of a mobile computed tomography system 1 in one embodiment of the present invention. The mobile computed tomography system 1 comprises a gantry 20 with an opening 21 into which a patient can be at least partially received for a computed tomography image data capture. The gantry 20 further comprises a housing 23 which accommodates a gantry frame 22 within it. Arranged in the gantry frame 22 on a rotor mounted able to rotate about a system axis z relative to the gantry frame 22 are imaging components, an X-ray tube R and an X-ray detector D. The X-ray tube R is oriented toward the X-ray detector D and emits X-ray radiation S in a fan shape in the direction of the X-ray detector D. During the image data capture, both the imaging components R, D and/or the rotor rotate about the body region of the patient located in the opening 21 and map it via a plurality of X-ray projections captured from different beam directions.

The X-ray projections can then be transferred to a computer and/or control unit ST of the CT system 1 for reconstruction of a three-dimensional representation of the body region.

The mobile CT system 1 further comprises a carriage 30 that can be moved with motor support over a substrate, typically the floor and/or flooring of a medical facility. For this purpose, the carriage 30 comprises a motor M, for example, a per se known electric motor which is operated via an energy storage medium such as, for example, a lithium ion battery B. The carriage 30 comprises a support frame 31 on which the chassis of the mobile CT system is arranged substantially oriented toward the substrate. Furthermore, the gantry 20 is arranged on an upper side of a support frame 31 of the carriage 30, that is, above the support frame 31. The carriage can further have an operating tower 32 in the housing of which, the control unit ST can preferably be accommodated and on which an operating interface for an operating person can be provided. The operating interface can comprise an operating element BE, herein in the form of an operating handle for steering a travel movement of the mobile CT system 1. The operating interface can comprise alternative and/or further operating, input or output elements such as, for example, a touch display or a microphone and/or a loudspeaker.

According to an embodiment of the present invention, the support frame 31 of the carriage 30 is designed comprising at least one shaped profile tube, as described below by reference to the following drawings.

Figure 2:
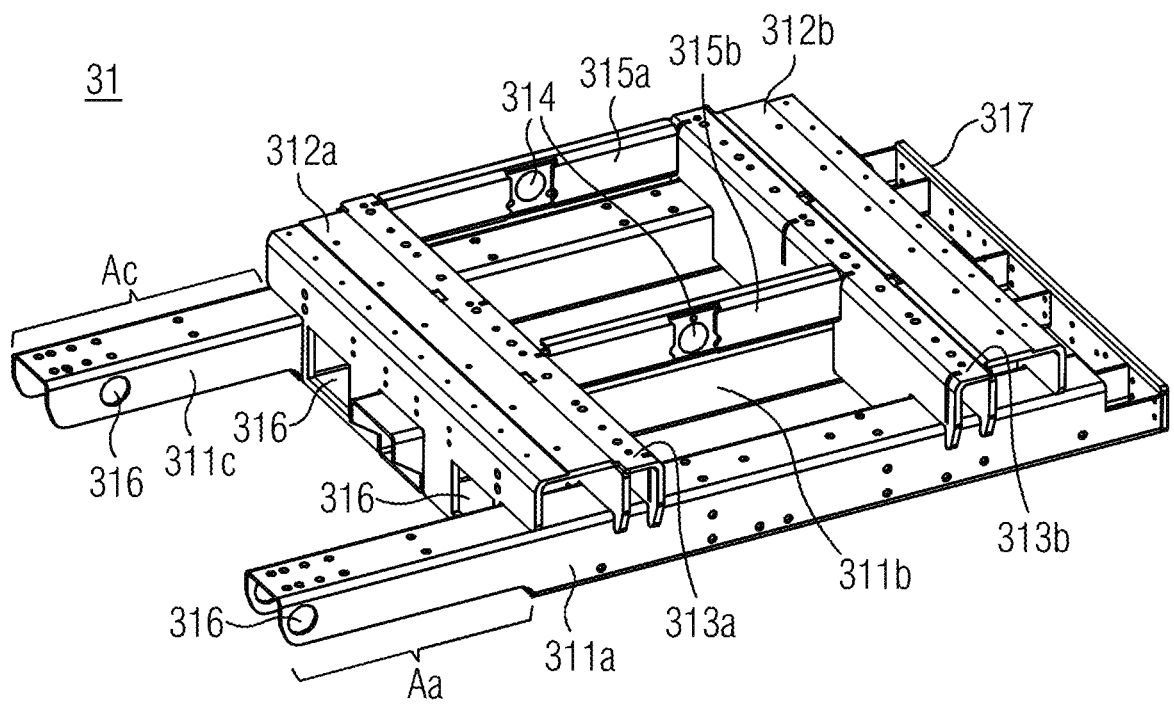
FIG. 2 shows a detailed view of a carriage of the mobile computed tomography system in one embodiment of the present invention.

FIG. 2 shows a detailed view of a carriage 30 of the mobile computed tomography system 1 in one embodiment of the present invention.

Figure 3:
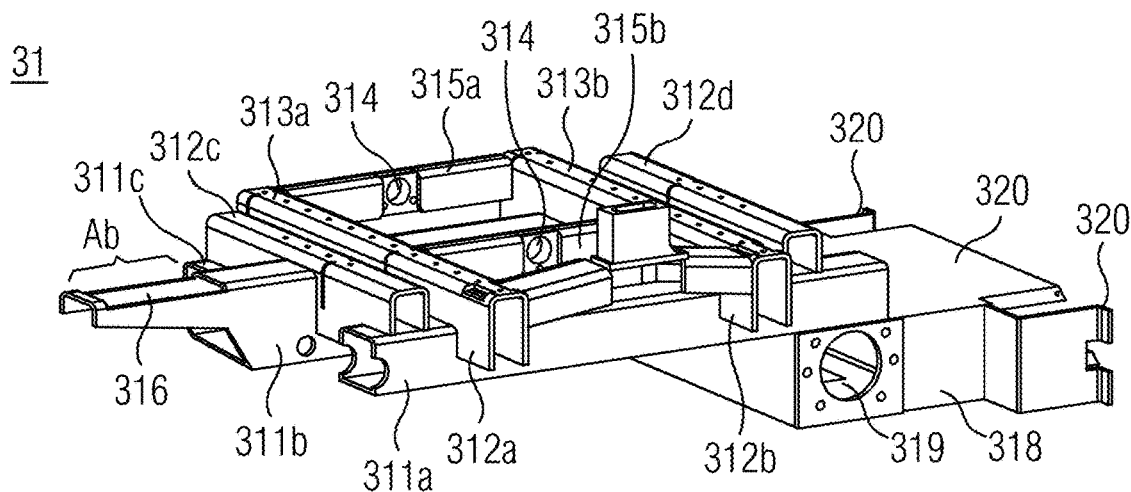
FIG. 3 shows a detailed view of a carriage of the mobile computed tomography system in another embodiment of the present invention.

FIG. 3 shows a detailed view of a carriage 30 of the mobile computed tomography system 1 in another embodiment of the present invention.

In both embodiments, the support frame 31 of the carriage 30 comprises three shaped profile tubes 311*a*, 311*b*, 311*c* extending parallel to and spaced apart from one another. These are oriented parallel to the advancing direction of the carriage, i.e. starting from the operating tower 32, they face in the direction of the front side of the mobile CT system 1. The three shaped profile tubes 311*a*, 311*b*, 311*c* are arranged in a plane above the substrate and have the same spacing from one another. The shaped profile tubes 311*a*, 311*b* and 311*c* are each designed as rectangular profile tubes, in this case specifically as square profile tubes.

The support frame 31 of the carriage 30 also comprises two further shaped profile tubes 312*a*, 312*b*, extending parallel to and spaced apart from one another via which the square profile tubes 311*a*, 311*b* and 311*c* are connected to one another. The shaped profile tubes 312*a*, 312*b* are each designed as U-profile tubes 312*a*, 312*b*. They can be post-processed particularly easily and, in particular, cut-outs can be introduced into the longitudinal sides of the U-profile tubes 312*a*, 312*b*, which are adapted to the shape of the square profiles 311*a*, 311*b* and 311*c*. Accordingly, in both embodiments, the U-profile tubes 312*a*, 312*b* are oriented with their open longitudinal sides downward, that is toward the substrate and both the U-profile tubes 312*a*, 312*b* extend above the square profile tubes 311*a*, 311*b* and 311*c*.

The shaped profile tubes are advantageously welded to one another at the contact sites.

This arrangement of the U-profile tubes 312*a*, 312 has the further advantage that the upwardly directed profile sides 313*a*, 313*b* of the U-profile tubes 312*a*, 312*b* are designed for receiving a linear guideway for which the gantry frame 22 carrying the imaging components R, D are designed. For example, linear guide rails can be screw fastened onto the post-processed contact surfaces 313a, 313b of the U-profile tubes 312a, 312b via a plurality of bores. Guide elements, for example, guide pins of the gantry frame 22 can engage in a precisely fitting manner into the guide rails. This has the result that the gantry frame 22 can be displaced along the U-profile tubes 312a, 312b relative to the carriage 30 and/or relative to the support frame 31. In this way, a movement of the imaging components R, D along the z-axis (=system axis) during an image data capture is advantageously enabled, wherein the entire mobile CT system 1 does not have to move. The present invention advantageously dispenses with an additional structure for realizing this function.

Advantageously, in both embodiments, further support areas for receiving further linear guideways are provided, via which in a similar manner, housing parts of the housing 23 engaging telescopically in one another can be guided linearly in order advantageously to extend the displacement travel for the gantry frame 22. In FIG. 2, these further support areas are also formed by the upwardly directed longitudinal sides 313a, 313b of the U-profile tubes 312a, 312b. In FIG. 3, the further support areas are also formed via additional U-profile tubes 312c, 312d.

In both the embodiments of FIGS. 2 and 3, the two U-profile tubes 312a, 312b are connected via two transverse struts 315a, 315b. They are also designed as shaped profile components. They each have a bearing bushing 314 placed centrally between the two U-profile tubes 312a, 312b for a per se known recirculating ball screw and/or a ball screw drive (not shown) for displacing the gantry frame 22. Via a ball screw drive comprising the recirculating ball screw, a pushing force can be applied to the gantry frame 22, so that it can be moved along the U-profile tubes 312a, 312b. Alternative drive concepts for the gantry frame 22 are always conceivable. Advantageously, the present invention utilizes the structural space freed up by the innovative support frame construction for integrating the gantry frame drive and/or enables a mounting of the gantry frame drive in components of the support frame 31.

Furthermore, at least one of the three rectangular profile tubes 311a, 311b, 311c forms at its end in the advancing direction of the carriage 30, a seating 316 for a wheel arrangement 322. A wheel arrangement 322 can therein comprise one or two wheel elements 324 and at least one holding element 323 with which the wheel elements 324 are fastened to the support frame 31.

For this purpose, in FIG. 2, the two outer square profile tubes 311a and 311c have forwardly protruding projections Aa, Ac in which seatings 316 in the form of bores for wheel suspension are provided. Furthermore, in FIG. 2, further wheel suspension seatings are provided in the U-profile tube 312a in order to bring about a stable binding of the wheel arrangement to the support frame 31.

In FIG. 3, the centrally extending square profile tube 311b has an also forwardly directed projection Ab which is designed tapering in a pointed manner and is provided with a milled-out seating 316 for a wheel suspension. The wheel arrangements arranged on the projections Aa, Ab, Ac are therefore front wheels of the mobile CT system 1.

For the fastening of rear wheels, arranged at each of the ends of at least two rectangular profile tubes 311a, 311c lying opposite the wheel arrangement seating 316 is a further seating 319 (see FIG. 3 and FIG. 6) for a further wheel arrangement (not shown), wherein the further wheel arrangement seatings 319 are constructed in a bent sheet metal element 318 for receiving a motor M of the carriage 30. As shown in FIG. 3, the bent sheet metal element can be designed and/or formed and fastened via corresponding contact surfaces beneath the ends of the square profile tubes 311a, 311c.

Figure 6:
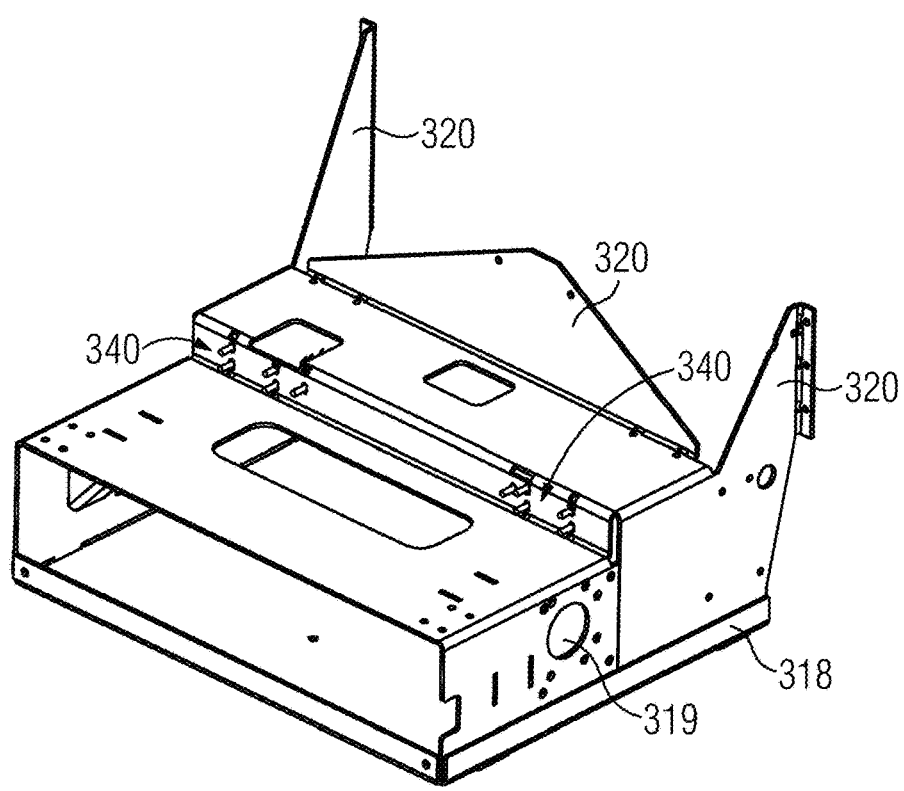
FIG. 6 shows a detailed view of a motor seating of a mobile computed tomography system in one embodiment of the present invention.

FIG. 6 shows a detailed view of an alternative bent sheet metal element 318 in the form of a motor seating in another embodiment of the mobile computed tomography system. Herein, the bent sheet metal element 318 has a modified base shape. In particular, via, inter alia, corresponding connecting elements, in this case screws 340, in embodiments of the support frame 31 shown in the embodiment of FIG. 2, said bent sheet metal element can be fastened, in particular both laterally via the contact surface 317 and also beneath the square profile tubes 311a, 311b, 311c.

In both the embodiments of the bent sheet metal element 318 shown in FIG. 2 or FIG. 6, it is designed to support a housing for receiving a control unit ST of the computed tomography system 1, specifically the operating tower 32. Accordingly, each variant of the bent sheet metal element 318 comprises different attachment elements 320 for connecting and/or attachment of the operating tower 32 to the bent sheet metal element 318.

Alternative design variants for the motor seating 318 and/or the attachment elements 320 are also possible.

Figure 4:
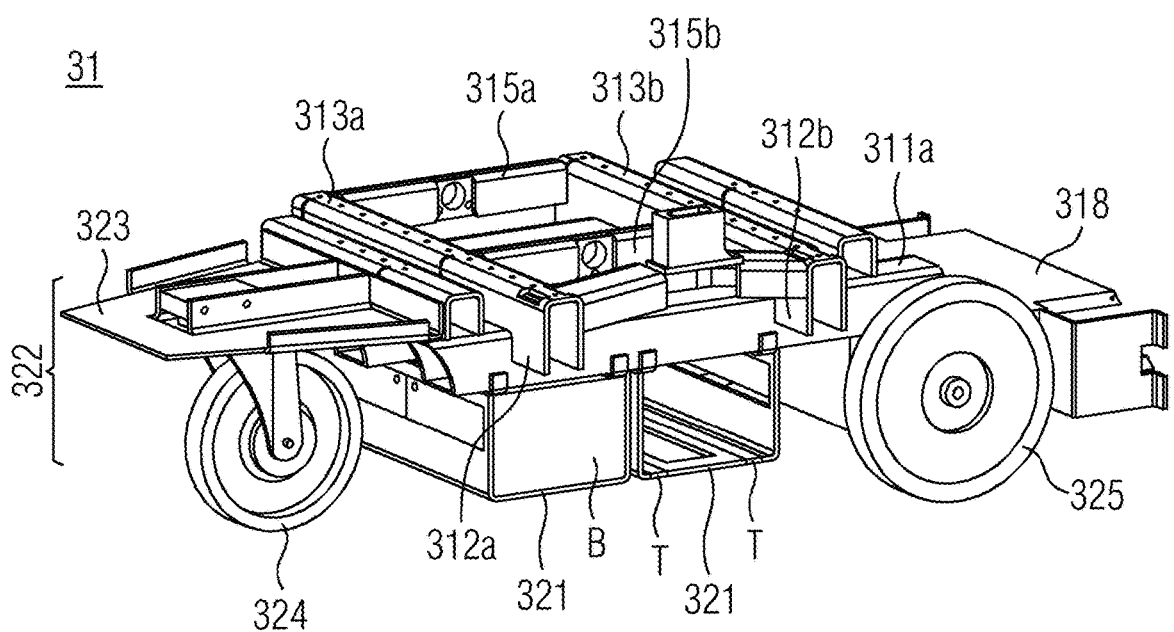
FIG. 4 shows a detailed view of the carriage of the mobile computed tomography system according to FIG. 3 with a first chassis embodiment and battery push-in compartments.
Figure 7:
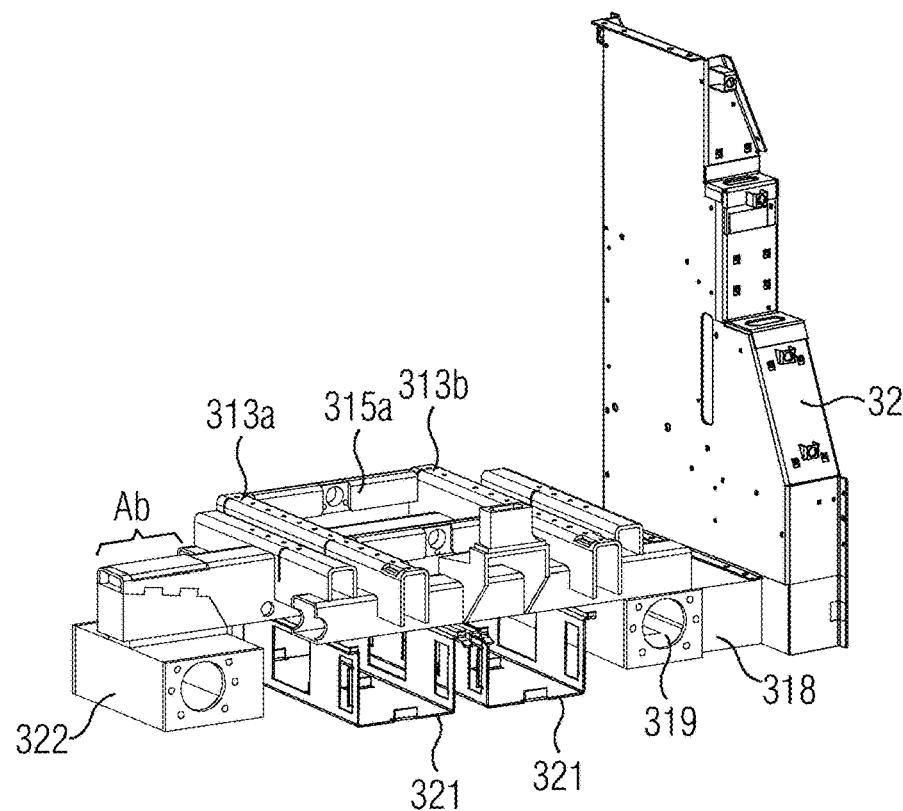
FIG. 7 shows a further detailed view of the carriage of the mobile computed tomography system according to FIG. 3.
Figure 8:
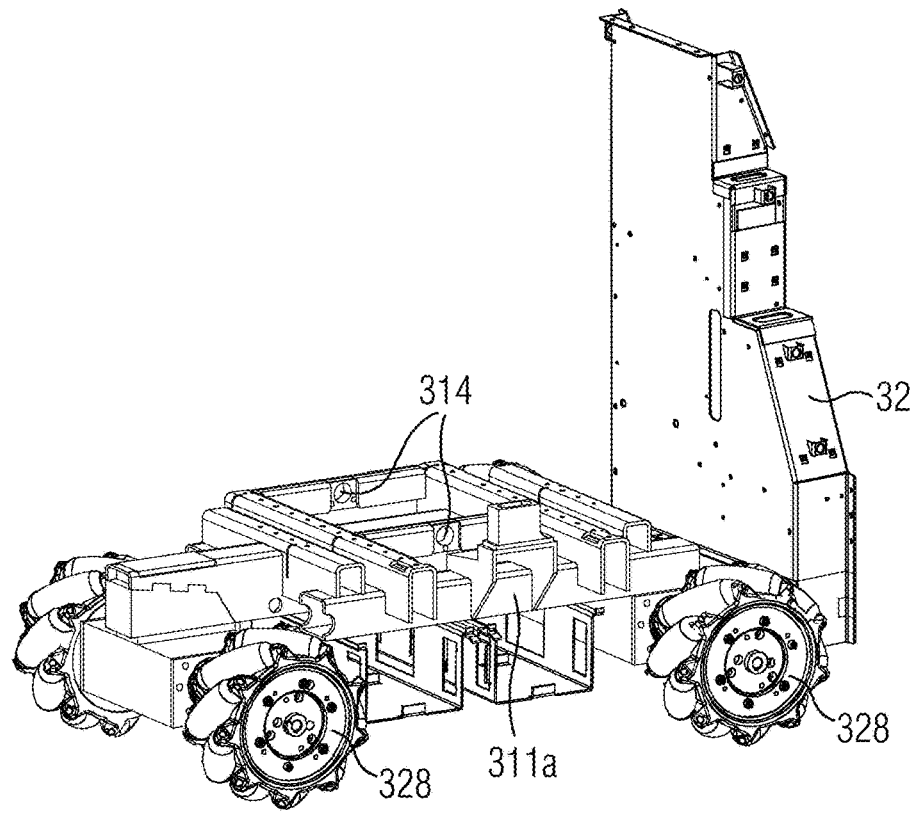
FIG. 8 shows a detailed view of the carriage of the mobile computed tomography system according to FIG. 3 with an alternative chassis embodiment.
Figure 9:
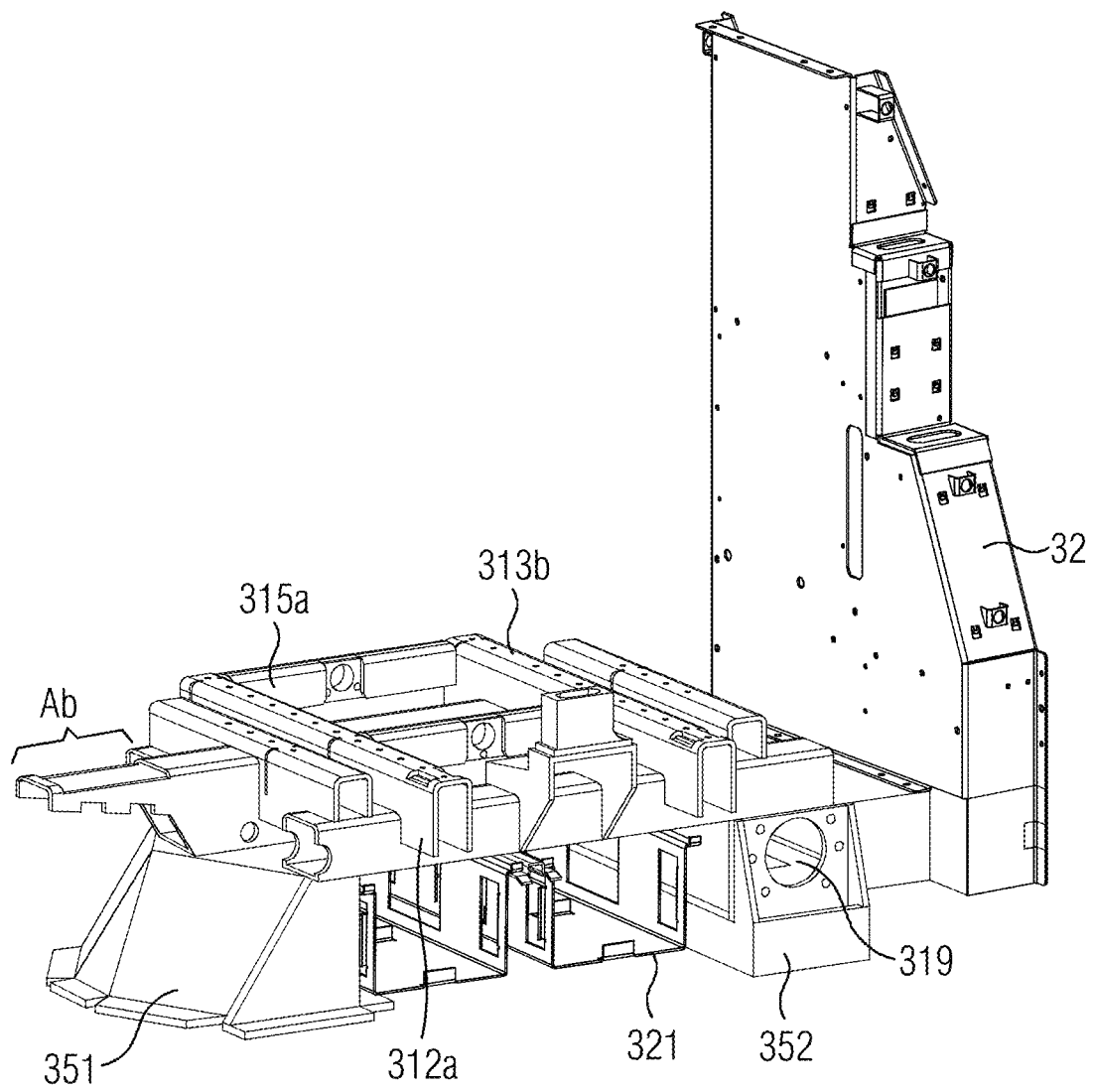
FIG. 9 shows a detailed view of the carriage of the mobile computed tomography system according to FIG. 3 in an embodiment able to be firmly mounted on a substrate.

FIG. 7, 8 or 9 also show the support frame 31 according to an embodiment of the present invention in accordance with FIG. 3 or 4 with a mounted motor seating 318 and a mounted operating tower 32.

Figure 10:
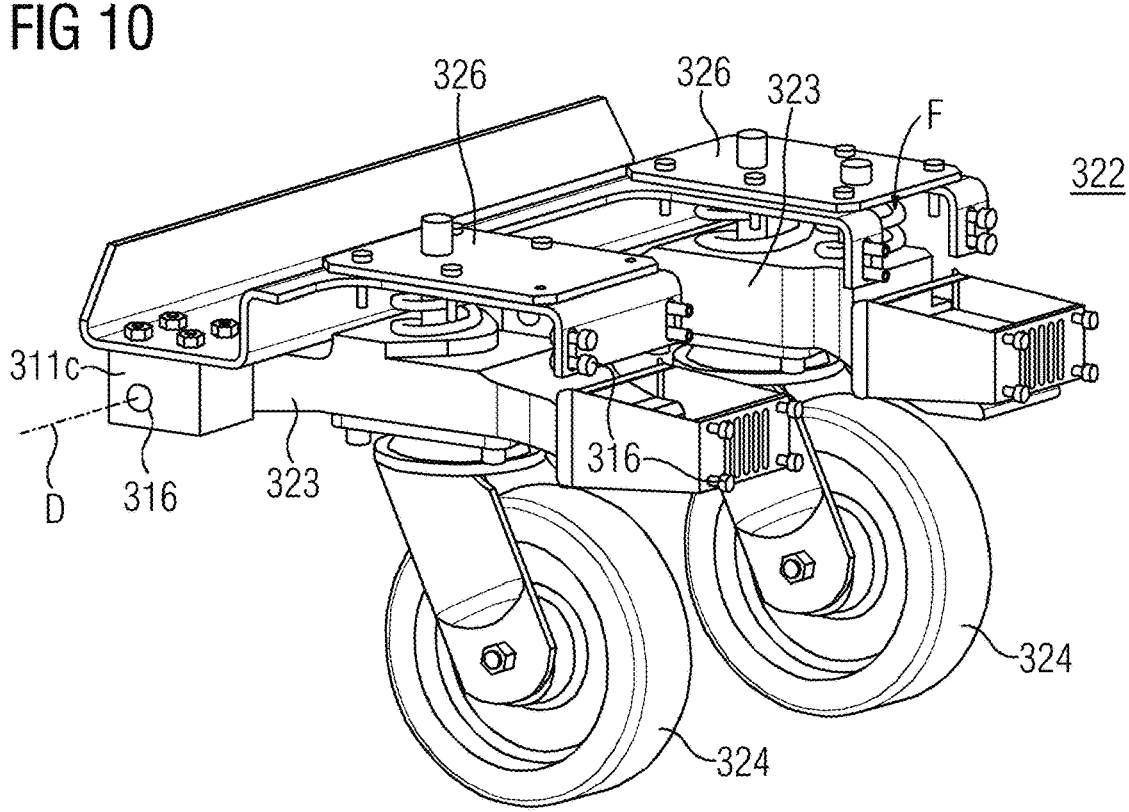
FIG. 10 shows a detailed view of a wheel arrangement according to the present invention with spring elements in one embodiment of the present invention.

FIG. 4 shows a detailed view of the carriage 30 of the mobile computed tomography system 1 according to FIG. 3 with a first chassis embodiment and battery drawer compartments 321. The wheel arrangement 322 shown here for configuring the front wheel comprises a holding element 323 arranged in the seating 316 of the square profile tube 311b, also configured as a bent sheet metal element to which a wheel element 324, in this case in the form of a tracking roller that can be blocked passively or actively, is arranged. In this embodiment, a motor torque is transferred only to the wheel elements 325 arranged in the rearward wheel suspension seatings 319 in the form of, for example, wheels driven via a differential drive. The tracking roller 324 follows accordingly. Alternatively, as shown in FIG. 10, via at least the square profile tubes 311a, 311c and corresponding suspension seatings 316 and two holding elements 323, two passive tracking rollers 324 can be provided. In this way, in particular, a more cost-effective linear maneuverability for the CT system 1 can be achieved.

FIG. 8 shows a detailed view of the carriage 30 of the mobile computed tomography system 1 in accordance with FIG. 3, having an alternative chassis embodiment. In this case, four identical wheel elements 328 in the form of omnidirectional wheels are provided, which are connected at the corresponding suspension seatings 316, 319 to the support frame 31 of the carriage 30. The omnidirectional wheels 328 are all designed to be active, that is capable of being driven, so that in this embodiment of the present invention, an areal movability can be achieved which is distinguished by an advantageously small turning circle and is in particular well suited to enclosed surroundings. Embodiments of the present invention with three omnidirectional wheels are also possible.

Not separately shown, but also within the meaning of the present invention is an embodiment of the CT system 1 comprising a wheel arrangement with an actively steerable roller within the meaning of a drive steering system. In this embodiment, the drive steering system is preferably configured as an active front wheel drive. The drive of the wheel element designed as a steerable roller is included here in the wheel arrangement which can be, for example, attached via the receptacles 316 on the support frame 31. In this embodiment, the two rear wheels are advantageously designed as passive wheels so that the now freed up structural space in the motor seating 318 can be used otherwise, for example by components of the operating tower 32.

FIG. 9 shows a detailed view of the carriage 30 of the mobile computed tomography system 1 in accordance with FIG. 3, in an embodiment that can be permanently mounted on a substrate. Herein, in place of wheel arrangements and/or in place of a chassis, further connecting elements designed as bent sheet metal elements 351, 352 are provided which provide contact surfaces and/or attachment points for anchoring the carriage to a substrate, for example, the floor of an ambulance. Apart from the further bent sheet metal elements 351, 352, the design of the support frame 31 does not differ from the design of the support frame for an adjustable embodiment according to the present invention.

Figure 5:
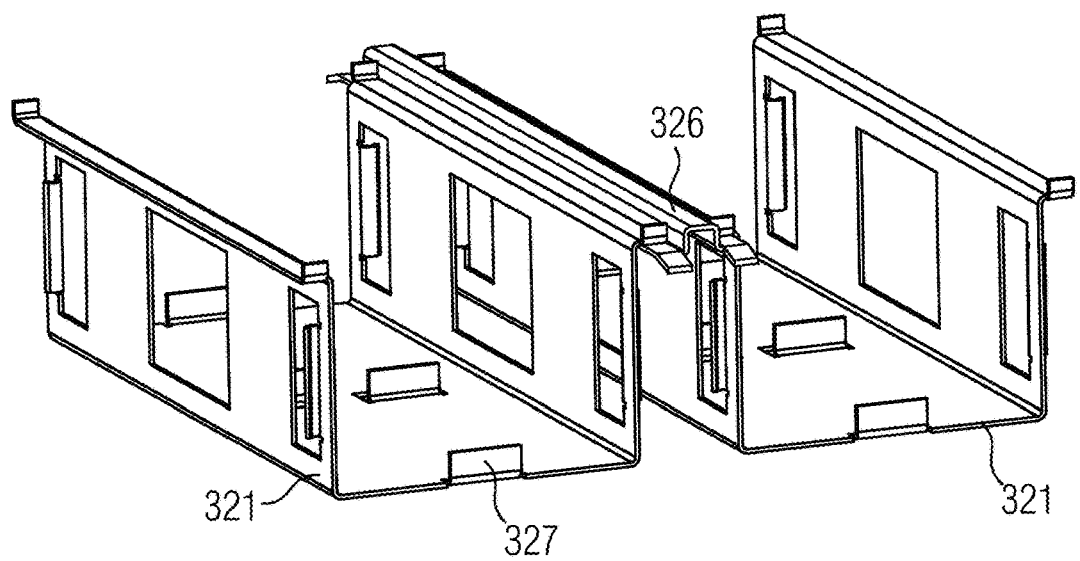
FIG. 5 shows a detailed view of a battery drawer in one embodiment of the present invention.

FIG. 4 and FIG. 5 each show detail views of at least one battery compartment 321 of the CT system 1 in different embodiments. Specifically, they show battery compartments 321 arranged beneath the rectangular profile tubes 311a, 311b, 311c for receiving a battery B for operating consumers of the CT system 1 such as, for example, the motor M and/or the control unit ST and/or the imaging components R, D etc. The battery compartments 321, in this case two being provided, are oriented transversely to the advancing direction of the carriage 30 and are accessible at least at one short side. Alternative arrangements in which one or more batteries are arranged, for example, with their longitudinal axis along the advancing direction are also possible. In both embodiments, the battery compartments 321 can comprise position securing elements 327 which can prevent slipping of the battery B due, for example, to vibrations during travel. In this way, a contact closure between poles of the battery and supply lines to the consumers of the CT system 1 is ensured at all times.

Whereas the battery compartments 321 in FIG. 4 are firmly installed as push-in compartments on the undersides of the square profile tubes 311a, 311b, 311c and permit the lateral pushing-in and/or the lateral removal of the battery B itself, the battery compartment 321 in FIG. 5 is designed as a battery drawer which can be pulled out laterally under the support frame. In the embodiment according to FIG. 4, for example, Teflon-coated rails T are provided in order to facilitate the removal and/or introduction of the battery. In the embodiment according to FIG. 5, the battery drawer 321 has at least one slide rail 326 which can also be coated with Teflon in order advantageously to be able to move the battery drawer along easily under the square profile tubes.

FIG. 10 shows a detailed view of a wheel arrangement 322 according to an embodiment of the present invention with a plurality of spring elements F in one embodiment of the present invention.

Figure 11:
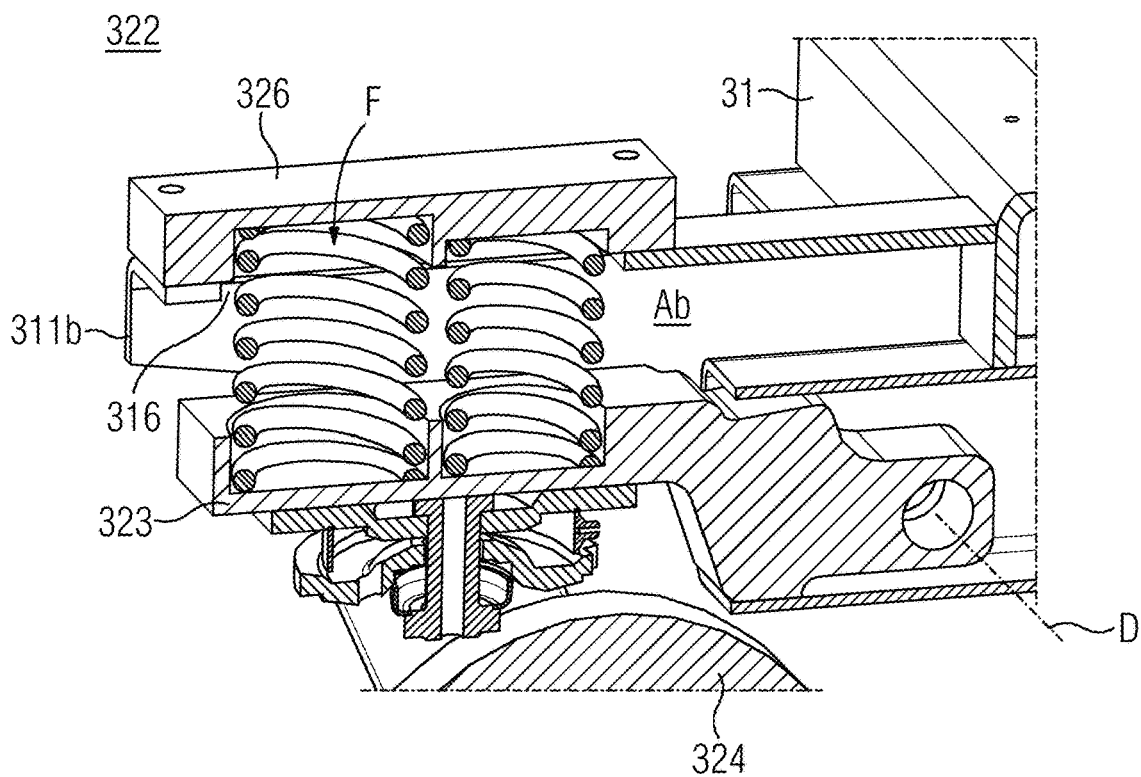
FIG. 11 shows a sectional view of a wheel arrangement according to the present invention with spring elements in a further embodiment of the present invention.

FIG. 11 shows a sectional view of a wheel arrangement 322 according to an embodiment of the present invention with spring elements F in a further embodiment of the present invention.

The spring elements advantageously serve, during travel, to compensate for unevenness of the substrate and to minimize loading on the carriage 30 due to travel-related vibrations. According to an embodiment of the present invention, the wheel elements 324 are mounted sprung via the spring elements relative to the support frame 31. This means the wheel elements 324 are pressed against the substrate by the spring elements F. By way of the intrinsic weight of the CT system 1, of approximately 1 metric ton, the spring element is tensioned and/or compressed. Unevenness in the substrate, both depressions and also elevations, are now compensated for by the spring elements F, and are no longer (completely) introduced into the support frame 31. In the embodiments shown, the spring elements F each comprise two helical springs per wheel element 324. In other embodiments, only one helical spring can be provided per wheel element 324.

Other embodiments of a spring element F are also conceivable, for example, in the case of an embodiment of the CT system permanently mounted on the substrate, the support frame 31 can be fastened to the substrate, for example, via a hexapod damping system in order to dampen vibrations caused by a travel movement of an ambulance.

In FIGS. 10 and 11, the spring elements F are supported between support elements 326 permanently connected to the support frame 31 and holding elements 323 which are attached to the support frame so as to be rotatable about a rotation axis D, to which holding elements the wheel elements 324 are fastened. Via the rotatable mounting of the holding elements 323, a compensation movement of the spring elements F is permitted which brings about a distance change between the wheel elements 324 and the support frame 31. In FIG. 11, the spring elements F are arranged such that they extend through the wheel suspension seating 316 of the projection Ab of the square profile tube 311b. Other arrangements of the spring elements are also conceivable.

Where it has not yet explicitly been stated, but is useful and in the spirit of the present invention, individual exemplary embodiments, individual sub-aspects or features thereof can be combined and/or exchanged with one another without departing from the scope of the present invention. Advantages of the present invention described in relation to an exemplary embodiment also apply, where transferrable, to other exemplary embodiments without this being explicitly stated.

The present invention is now summarized briefly as follows. The present invention realizes a modular design for a carriage of a mobile CT system 1 using ready-made and therefore inexpensive semifinished products such as shaped profile parts and steel sheet. With a material and space-saving design, costs can be reduced overall. By way of the matching of interfaces, the support frame design can be utilized again in many ways without adaptations. In this way, development time and costs can be reduced. This also makes possible the retrofitting of mobile CT systems in the field.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of the embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing embodiments. The present invention may, however, be embodied in many alternate forms and should not be construed as limited to only the embodiments set forth herein.

What is claimed is:

1. A mobile computed tomography system, comprising:
   a gantry having an opening to at least partially accommodate a patient; and
   a carriage configured to move over a substrate with motor assistance, wherein
   the gantry is arranged on an upper side of a support frame of the carriage,
   the support frame includes three shaped profile tubes extending parallel to, and being spaced from, one another, and
   the three shaped profile tubes are oriented parallel to an advancing direction of the carriage.

2. The mobile computed tomography system as claimed in claim 1, wherein the three shaped profile tubes are connected via two further shaped profile tubes extending parallel to, and being spaced from, one another.

3. The mobile computed tomography system as claimed in claim 2, wherein the three shaped profile tubes have a rectangular profile and the two further shaped profile tubes have a U-profile.

4. The mobile computed tomography system as claimed in claim 3, wherein the two further shaped profile tubes are arranged above the three shaped profile tubes and with a longitudinal side open toward the substrate.

5. The mobile computed tomography system as claimed in claim 4, wherein upwardly directed profile sides of the two further shaped profile tubes are configured to receive a linear guideway for a gantry frame carrying imaging components of the gantry, wherein the gantry frame is configured to be displaced, relative to the carriage, along the two further shaped profile tubes.

6. The mobile computed tomography system as claimed in claim 5, wherein the two further shaped profile tubes are connected via at least two transverse struts, each of the at least two transverse struts forming, centrally between the two further shaped profile tubes, a bearing bushing for a recirculating ball screw for displacing the gantry frame.

7. The mobile computed tomography system as claimed in claim 5, wherein at least one of the three shaped profile tubes forms a seating for a wheel arrangement at an end in the advancing direction of the carriage.

8. The mobile computed tomography system as claimed in claim 5, further comprising:
   at least one battery compartment beneath the three shaped profile tubes, the at least one battery compartment being configured to receive a battery, and the at least one battery compartment being oriented transversely to the advancing direction of the carriage and being accessible on at least one short side.

9. The mobile computed tomography system as claimed in claim 4, wherein the two further shaped profile tubes are connected via at least two transverse struts, each of the at least two transverse struts forming, centrally between the two further shaped profile tubes, a bearing bushing for a recirculating ball screw for displacing a gantry frame.

10. The mobile computed tomography system as claimed in claim 4, wherein at least one of the three shaped profile tubes forms a seating for a wheel arrangement at an end in the advancing direction of the carriage.

11. The mobile computed tomography system as claimed in claim 4, further comprising:
    at least one battery compartment beneath the three shaped profile tubes, the at least one battery compartment being configured to receive a battery, and the at least one battery compartment being oriented transversely to the advancing direction of the carriage and being accessible on at least one short side.

12. The mobile computed tomography system as claimed in claim 3, wherein the two further shaped profile tubes are connected via at least two transverse struts, each of the at least two transverse struts forming, centrally between the two further shaped profile tubes, a bearing bushing for a recirculating ball screw for displacing a gantry frame.

13. The mobile computed tomography system as claimed in claim 12, further comprising:
    at least one battery compartment beneath the three shaped profile tubes, the at least one battery compartment being configured to receive a battery, and the at least one battery compartment being oriented transversely to the advancing direction of the carriage and being accessible on at least one short side.

14. The mobile computed tomography system as claimed in claim 3, wherein at least one of the three shaped profile tubes forms a seating for a wheel arrangement at an end in the advancing direction of the carriage.

15. The mobile computed tomography system as claimed in claim 14, wherein the wheel arrangement comprises at least one wheel element configured as at least one of a passive wheel element or a driven wheel element.

16. The mobile computed tomography system as claimed in claim 15, wherein the at least one wheel element is an omnidirectional wheel.

17. The mobile computed tomography system as claimed in claim 14, wherein the wheel arrangement comprises at least one spring element configured to support a wheel element against the support frame.

18. The mobile computed tomography system as claimed in claim 14, wherein a further seating for a wheel arrangement is arranged on each of the ends, lying opposite to the seating for the wheel arrangement, of at least two of the three shaped profile tubes, wherein the further seating is constructed in a bent sheet metal element for receiving a motor, wherein the bent sheet metal element is configured to carry a housing to receive a control unit of the mobile computed tomography system.

19. The mobile computed tomography system as claimed in claim 3, further comprising:
    at least one battery compartment beneath the three shaped profile tubes, the at least one battery compartment being configured to receive a battery, and the at least one battery compartment being oriented transversely to the advancing direction of the carriage and being accessible on at least one short side.

* * * * *